United States Patent
Wieringa et al.

(10) Patent No.: US 11,583,617 B2
(45) Date of Patent: Feb. 21, 2023

(54) DIALYSIS DEVICE AND A CONTROL SYSTEM FOR BLOOD DIALYSIS

(71) Applicant: STICHTING IMEC Nederland, AE Eindhoven (NL)

(72) Inventors: Fokko Wieringa, Leuven (BE); Mario Konijnenburg, Leuven (BE)

(73) Assignee: STICHTING IMEC NEDERLAND, Eindhoven (NL)

( * ) Notice: Subject to any disclaimer, the term of this patent is extended or adjusted under 35 U.S.C. 154(b) by 614 days.

(21) Appl. No.: 16/678,470

(22) Filed: Nov. 8, 2019

(65) Prior Publication Data

US 2021/0138132 A1 May 13, 2021

(51) Int. Cl.
*A61M 1/16* (2006.01)
*A61M 1/30* (2006.01)

(52) U.S. Cl.
CPC .......... *A61M 1/1605* (2014.02); *A61M 1/304* (2014.02); *A61M 1/305* (2014.02); *A61M 2202/0021* (2013.01); *A61M 2202/0413* (2013.01); *A61M 2230/205* (2013.01); *A61M 2230/207* (2013.01)

(58) Field of Classification Search
CPC ...... A61M 1/16; A61M 1/1605; A61M 1/304; A61M 1/305; A61M 1/3681; A61M 2202/0021; A61M 2202/0413; A61M 2202/0445; A61M 2202/07; A61M 2205/054; A61M 2230/205; A61M 2230/207
See application file for complete search history.

(56) References Cited

U.S. PATENT DOCUMENTS

| | | |
|---|---|---|
| 2014/0246367 A1 | 9/2014 | Jankowski et al. |
| 2015/0335811 A1 | 11/2015 | Jankowski et al. |
| 2015/0343134 A1 | 12/2015 | Tschulena et al. |

FOREIGN PATENT DOCUMENTS

EP 0577026 A2 1/1994

OTHER PUBLICATIONS

Partial European Search Report, EP Application No. EP20205485, dated Mar. 18, 2021.
Hayashi: "Fundamental Studies on the Electrical Potential Difference Across Blood Vessel Walls and Applications of Direct Current Coagulation", Nagoya Journal of Medical Science, vol. 30, pp. 399-418, 1968.

*Primary Examiner* — Dirk R Bass
(74) *Attorney, Agent, or Firm* — Moser Taboada

(57) ABSTRACT

A dialysis device (100) comprises: a dialyzer for exchange of substances between a blood flow and a dialysate flow in a dialysis area (106) of the dialyzer, wherein the dialyzer comprises a dialyzer membrane (110) for passing toxins in the blood flow to the dialysate flow through pores (112) of the dialyzer membrane (110); and a capacitively coupled generator (120) for generating electromagnetic fields in the dialysis area (106) for loosening electrostatic bonds between toxins and proteins in the blood flow, wherein the generator (120) is capacitively coupled to the blood flow and to the dialysate flow on opposite sides of the dialyzer membrane, and wherein the dialysate membrane (110) is formed of a material having lower conductance than blood and dialysate such that a large electromagnetic field strength is provided across the pores (112) of the dialyzer membrane (110).

17 Claims, 1 Drawing Sheet

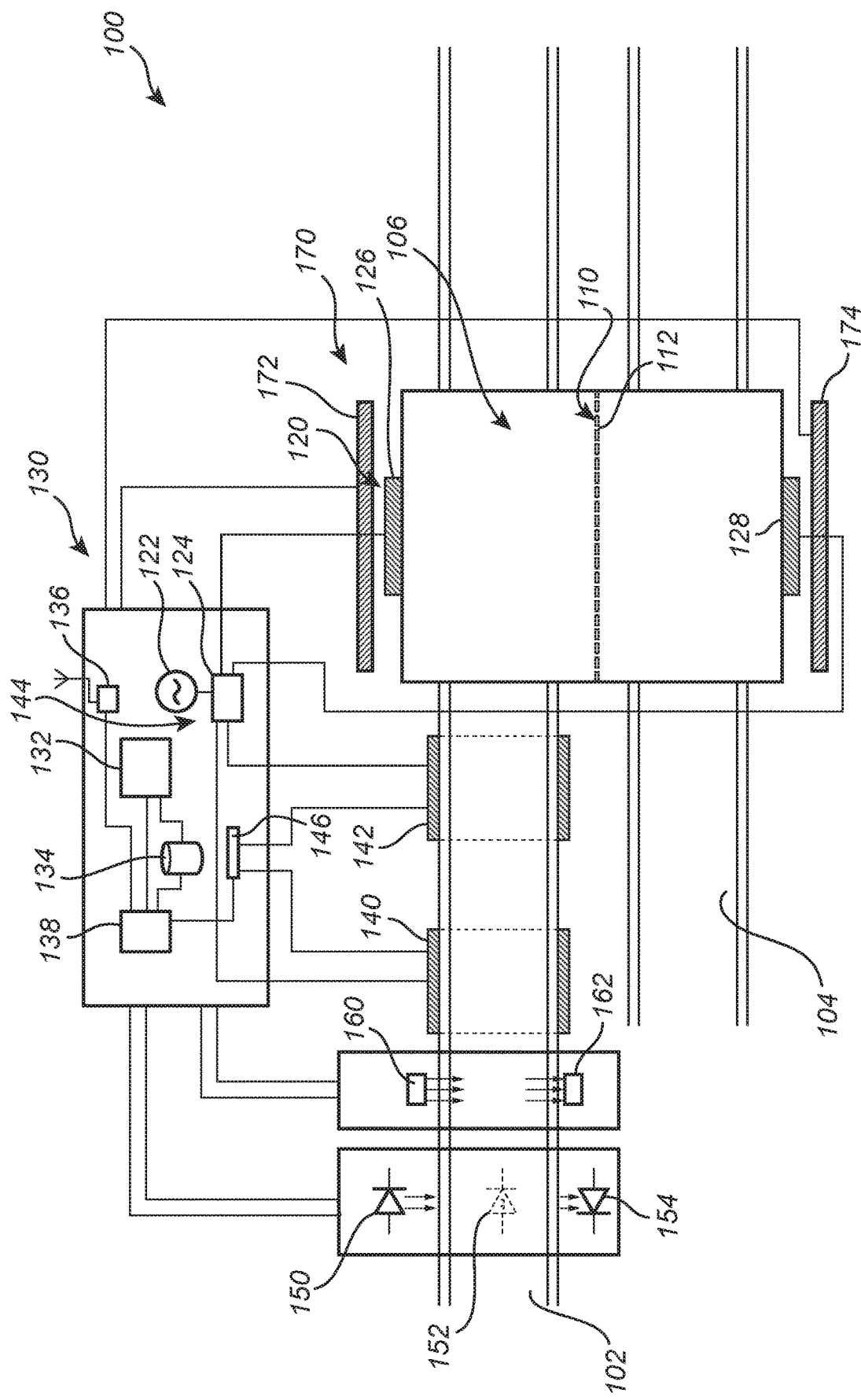

DIALYSIS DEVICE AND A CONTROL SYSTEM FOR BLOOD DIALYSIS

TECHNICAL FIELD

The present inventive concept relates to blood dialysis devices.

BACKGROUND

Patients suffering from renal failure are dependent on dialysis to provide filtering toxins from the blood flow. The function of the kidneys needs to be artificially provided regularly in order to avoid in poisoning and death of the patients.

Thus, patients may require dialysis procedures frequently. The dialysis procedure is time consuming and highly affects life of the patients and is also associated with high costs for society. In this respect, it is important that dialysis is efficient in order to improve health of the patients.

A dialysis device typically includes a membrane through which fluid exchange between blood flow and a dialysate flow is provided. The function of the membrane is to allow toxins to pass through pores of the membrane so as to remove toxins from the blood flow. The membrane may allow filtering of toxins through the membrane based on a size of the pores. However, the toxins may be electrostatically bound to proteins in the blood flow. Since proteins may be of a larger size than the toxins, this may prevent a high percentage of the toxins to be removed from the blood flow such that the dialysis is inefficient.

In US 2015/0335811 a dialysis device is disclosed comprising a dialysis circuit, a blood circuit and a dialyzer, wherein the dialysis device has means for generating a high-frequency electromagnetic field and means for generating an electrostatic direct current field, wherein both means are arranged in such a way that blood to be treated can be exposed to the high-frequency electromagnetic field and the electrostatic direct current field when passing through the dialyzer. The high-frequency electromagnetic field may reduce strength of the electrostatic bonds between toxins and proteins. By using the electromagnetic field during dialysis, the portion of protein-bound toxins can be greatly reduced, such that toxins can be dialyzed to a greater extent and more effectively.

However, efficiency of the dialysis may still be further improved.

SUMMARY

It is an object of the present inventive concept to provide an efficient dialysis of toxins from blood flow. It is a further object of the present inventive concept to enable efficient control of dialysis, wherein the control may be based on monitoring of various parameters of blood flow.

These and other objects of the present inventive concept are at least partly met by the invention as defined in the independent claims. Preferred embodiments are set out in the dependent claims.

According to a first aspect, there is provided a dialysis device comprising: a dialyzer for exchange of substances between a blood flow and a dialysate flow in a dialysis area of the dialyzer, wherein the dialyzer comprises a dialyzer membrane for passing toxins in the blood flow to the dialysate flow through pores of the dialyzer membrane; and a capacitively coupled generator for generating electromagnetic fields in the dialysis area for loosening electrostatic bonds between toxins and proteins in the blood flow, wherein the generator is capacitively coupled to the blood flow and to the dialysate flow on opposite sides of the dialyzer membrane, and wherein the dialysate membrane is formed of a material having lower conductance than blood and dialysate such that a large electromagnetic field strength is provided across the pores of the dialyzer membrane.

The dialysis device is configured to provide a strong electromagnetic field close to the pores of the dialyzer membrane. This implies that the dialysis device is adapted to provide a function of loosening electrostatic bonds between toxins and proteins at and around the pores of the dialyzer membrane, such that the toxins are separated from proteins at the very location where the toxins are to pass from the blood flow to the dialysate flow. Thus, the dialysis device may ensure that the toxins are passed from blood flow to the dialysate flow and that the toxins are not bound to proteins when the toxins need to pass through membrane pores.

Since the material of the dialyzer membrane has lower conductance than blood and dialysate, the electromagnetic field in the dialysis area will be particularly strong across the membrane. The dialyzer membrane may be formed from a non-conducting or semiconductor material.

A large electromagnetic field strength being provided across the pores of the membrane should be construed as the electromagnetic field strength across the pores being larger than in blood and dialysate at the dialysis area. A field strength of 100 V/m may for instance be provided at the pores of the dialyzer membrane.

Thanks to the generator being capacitively coupled to the blood flow and dialysate flow, the generator is not in direct contact with blood flow and/or dialysate flow. This implies that sterility is not compromised. For instance, the capacitive coupling may be provided based on electrodes being arranged externally to flow circuitry in which blood flow and dialysate flow is provided. The capacitive coupling may be provided through walls of the flow circuitry.

The generator may be provided with two couplers, which are arranged at opposite sides in relation to the dialyzer membrane. For instance, each of the couplers may be attached to or arranged at a wall surrounding the dialysis area. The couplers may be implemented e.g. as coils, electrodes or capacitors.

The generator may be tuned to provide electromagnetic fields in a wide frequency range. The generator may be configured to provide electro-magnetic fields within a range of 100 kHz to 1 GHz, for example from 10 MHz to 500 MHz. In some embodiments, the generator may be configured to provide electro-magnetic fields within a range of 80 MHz to 170 MHz.

The generator may be configured to vary the frequency during dialysis. The generator may thus be a tunable generator. This may be useful for ensuring that electrostatic bonds between toxins and proteins are loosened.

However, the generator may also or alternatively be used for providing a constant frequency of the electromagnetic field. This may be useful if a particular frequency is determined to provide optimal loosening of the electrostatic bonds between toxins and proteins.

According to an embodiment, the dialysis device further comprises two capacitive electrodes which are configured for capacitive coupling to the blood flow through a wall of a blood flow channel configured to pass the blood flow therethrough, a generator which is configured for generating an AC voltage between the two capacitive electrodes, and an impedance measurement circuit, which is configured for measuring an impedance between the two electrodes at a plurality of frequencies, the measured impedances being indicative of a conductivity of blood.

Thanks to the use of capacitive electrodes, an impedance measurement may be performed without requiring contact between the electrodes and the blood flow. Thus, sterility is not compromised by the measurement and the electrodes may be easily re-used.

The measuring of impedances at a plurality of frequencies may allow an impedance spectroscopy measurement to be performed. The impedance spectroscopy measurement may be used for determining a concentration of ions in the blood based on the determined conductivity. For instance, a sodium ion concentration in the blood may be determined.

The generator may be configured to generate a tunable frequency AC voltage for enabling an impedance spectroscopy measurement to be performed. For instance, the frequency of the AC voltage may be tuned in a range of 40 Hz to 110 MHz.

The capacitive electrodes may be configured to be arranged in various relations to the blood flow channel.

For instance, the capacitive electrodes may be arranged on opposite sides of a cross-section of the blood flow channel. Thus, a conductivity of blood may be measured across a cross-section of the blood flow channel. This arrangement may be achieved e.g. by providing an annular carrier, which may be arranged around the blood flow channel, wherein the electrodes are arranged on diametrically opposite locations of the annular carrier to be arranged on opposite sides of the cross-section of the blood flow. The annular carrier may be provided with a releasable lock such that the annular carrier may e.g. be clipped on the blood flow channel. Alternatively, each of the electrodes is separately arranged in relation to the blood flow channel, e.g. by using an adhesive surface that is attached to the blood flow channel.

According to an alternative, the capacitive electrodes are arranged at different positions in relation to the blood flow, one electrode being downstream to another electrode. Thus, a conductivity may be measured along a direction of the blood flow. Each of the electrodes may be arranged in relation to the blood flow channel as described above, e.g. using an annular carrier or using an adhesive surface for attaching the electrode to the blood flow channel. Both electrodes may be arranged on a common annular carrier, wherein the annular carrier is configured to extend along a longitudinal direction of the blood flow channel and wherein the electrodes are spaced apart in the longitudinal direction on the annular carrier. Alternatively, each electrode is arranged on a separate annular carrier.

As used herein, "blood flow channel" should be construed as any hollow passageway through which a blood flow may be passed. The blood flow channel may comprise walls defining the passageway through the channel. For instance, the blood flow channel may be provided as a flexible tubing.

According to an embodiment, the dialysis device further comprises a first light source, which is configured to emit first light into the blood flow channel, wherein the emitted light is directed towards a light detector, which is arranged on an opposite side of the blood flow channel from the first light source, the light detector being configured to detect first light from the light source being diffusely transmitted through the blood flow, a second light source, which is configured to emit second light into the blood flow channel, wherein the second light source is arranged in relation to the light detector and the blood flow channel such that only scattered second light reaches the light detector, and a processor, which is configured to determine blood hematocrit and/or blood oxygenation levels based upon detected first light being diffusely transmitted and detected second light being scattered with compensation for an ion concentration in the blood based on the measured impedance.

The dialysis device may thus enable measuring of scattered light and transmitted light through the blood flow, wherein intensity of scattered light in relation to intensity of diffusely transmitted light may be used for determining a concentration of particles in the blood flow, such that a blood hematocrit level and/or a blood oxygenation level may be determined.

The scattering of light may be relatively independent on what type of particle is scattering light, whereas diffuse transmittance may be dependent on whether the light is absorbed by a specific type of particle. Thus, by selecting a wavelength of the first light to coincide with a high absorption of a specific type of particle of interest, the relation between the scattered light and the diffusely transmitted light may be used for determining a concentration of a specific type of particle in the blood flow. For instance, this may be used for determining a blood hematocrit level and/or a blood oxygenation level.

The first light and the second light may use a common wavelength, such that the detection of first light and second light may be performed sequentially. However, since intensity of scattering of light may be relatively similar for different wavelengths, the second light may use a different wavelength than the first light. In such case, the light detector may also comprise two different light-detecting elements associated with different filters, such that the diffusely transmitted first light and the scattered second light may be detected simultaneously.

For detection of blood hematocrit level and/or blood oxygenation level, the first light may for instance be a wavelength in a range of 630-670 nm and the second light may for instance be a wavelength in a range of 800-980 nm.

The detected light may be affected by a concentration of ions in the blood. In particular, a concentration of sodium may affect the measurements of intensity of light incident on the light detector. Thanks to the measurement of ion concentration using the impedance measurement circuit, an indication of ion concentration may be determined, which may be used as a compensation factor in determining blood hematocrit level and/or blood oxygenation level and/or other particle concentrations in blood. Similarly, the measured intensity of light incident on the light detector may also be used as compensation for accurately determining the ion concentration based on the measured impedances.

The light detector may be configured to detect an intensity of light incident on the light detector. The light detector may thus comprise a single photo-sensitive area, which may convert an intensity of incident light to an electrical signal for reading out the intensity of light. However, the light detector may comprise a plurality of photo-sensitive areas, which may be associated with different filters for detecting intensity of incident light of different wavelengths.

The first and second light sources may be light-emitting diodes (LEDs), which may be configured to emit light of a relatively narrow wavelength. When the first and second light is of a common wavelength, a single LED may be used and may be associated with different waveguides for providing emission of light from different positions into the blood flow channel.

The first light source and the light detector may be arranged on opposite sides of a cross-section of the blood flow channel. This arrangement may be achieved e.g. by providing an annular carrier, which may be arranged around the blood flow channel, wherein the first light source and the light detector are arranged on diametrically opposite locations of the annular carrier to be arranged on opposite sides of the cross-section of the blood flow. The annular carrier may be provided with a releasable lock such that the annular carrier may e.g. be clipped on the blood flow channel.

Alternatively, each of the first light source and the light detector is separately arranged in relation to the blood flow channel, e.g. by using an adhesive surface that is attached to the blood flow channel. The second light source may also be arranged on the annular carrier or may be separately arranged in relation to the blood flow channel. The second light source may be arranged in relation to the first light source such that a propagation direction of a light beam of the first light will be perpendicular to a propagation direction of a light beam of the second light. However, it should be understood that the propagation directions of the light beams need not be exactly perpendicular. It may be sufficient that the second light source is arranged such that the light beam of the second light is not incident on the light detector and that only second light being scattered into propagating in a different direction will reach the light detector.

The first and second light sources and the light detector may also be used for detecting optical absorption and/or scattering of light at a plurality of different wavelengths, e.g. in ranges of ultraviolet light, visible light and/or infrared light. The detected light intensities may be used for determining concentration levels of various different particles and/or substances in the blood flow. The first and second light sources may in this respect emit broadband wavelengths of light and the light detector may comprise filters for detecting intensities of respective wavelengths of light. Alternatively, a wavelength of light emitted by the first and/or the second light source may be tuned for sequentially emitting different wavelengths of light.

According to an embodiment, the generator for generating electromagnetic fields for loosening electrostatic bonds between toxins and proteins in the blood flow and the generator which is configured for generating an AC voltage between the two capacitive electrodes use a common oscillator.

By using a common oscillator for the generator for generating electromagnetic fields for loosening electrostatic bonds between toxins and proteins in the blood flow and the generator for generating an AC voltage for an impedance measurement, there is no need to have two separate oscillators. This enables a compact and cheap system for generating the desired signals.

The dialysis device may also use a common control circuit for generating a desired signal from the common oscillator. The common control circuit may thus be controlled for generating either a suitable electromagnetic field for loosening electrostatic bonds between toxins and proteins or for generating a suitable AC voltage for the impedance measurement.

The signal generated based on the common oscillator may be time-multiplexed. It may not be necessary to continuously perform impedance measurements and provide loosening electrostatic bonds between toxins and proteins. Rather, the impedance measurement may for instance be performed intermittently. For instance, the impedance measurement may be performed with a duration of 1 s having 30 s intervals between subsequent measurement periods. During the intervals between subsequent measurement periods, the signal for generating electromagnetic fields for loosening electrostatic bonds between toxins and proteins may be provided.

However, it should be realized that circuitry for generating the electromagnetic fields for loosening electrostatic bonds between toxins and proteins and circuitry for generating the AC voltage for the impedance measurement may be completely separate.

According to an embodiment, the dialysis device is configured for being worn on or implanted in a human body.

The dialysis device of the first aspect may be particularly suited for being worn on or implanted in a human body. The use of the electromagnetic field for loosening electrostatic bonds between toxins and proteins at or around the pores of the dialyzer membrane enables the dialysis device to efficiently remove toxins from the blood flow of a patient.

The use of a dialysis device that is worn on or implanted in the human body may have a large impact on life quality of the patient. The patient may no longer need to visit a hospital several times a week for receiving dialysis treatment. Also, with a largely reduced number of hospital visits, demands on hospital resources may be greatly reduced.

Thanks to the dialysis device being able to not only perform efficient dialysis, but also being able to perform one or more measurements on parameters of the blood, the blood may be continuously monitored to monitor health of the patient. This may be used for providing alerts when there is a need to visit a doctor and/or to control the dialysis so as to change parameters of the dialysis in view of the measurements performed. For instance, a speed of blood flow through the dialysis area may be controlled, e.g. in dependence of a blood hematocrit level to avoid that fluid extraction is performed too quickly giving too thick blood.

The dialysis device may thus be self-controlled based on measurements performed by the dialysis device so as to ensure efficient dialysis.

The dialysis device may comprise an inlet channel, which may be configured to be attached to an artery of the human being. The inlet channel may thus receive a blood flow to be provided to the blood flow channel of the dialysis device and to pass the dialysis area.

The dialysis device may further comprise an outlet channel, which may be configured to be attached to a vein of the human being. The outlet channel may be configured to receive blood flow having passed the dialysis area and may thus be configured to pass the filtered blood back to the venous blood flow of the human being.

The dialysis device may further comprise a waste outlet channel, which may be configured to receive waste products from the dialysate flow so as to remove toxins from the dialysis device. When the dialysis device is implanted in a human body, the waste outlet channel may be configured to be connected to the bladder. When the dialysis device is to be worn on the human body, the waste outlet channel may be connected to a collecting container, which may be worn on the human body and which may be regularly emptied.

According to an embodiment, the dialysis device further comprises a DC generator, which is configured for generating an electrostatic direct current field between the blood flow in the dialyzer and the human body, where a negative electrode of the DC generator is configured to be arranged at a blood flow side of the dialyzer and a positive electrode of the DC generator is configured to be arranged in contact with the human body.

The use of an electrostatic direct current field may prevent coagulation of blood. Blood components, such as platelets, red blood cells and white blood cells may be negatively charged, and the negative charge may be used by the body for holding the blood components at an injury site to cause coagulation. By providing an electrostatic direct current field in the blood flow of the dialysis device, blood components may be forced to move with the blood flow so as to prevent coagulation of blood in the blood flow of the dialysis device. This may be particularly useful to avoid clogging of blood flow channels of the dialysis device.

The use of the electrostatic direct current field may be particularly advantageous when the dialysis device is to be worn on or implanted in a human body, since the dialysis device is to be used for a long period of time. However, it should be realized that the electrostatic direct current field may also be used with other dialysis devices.

The electrostatic direct current field may be configured to provide a potential difference in a range of 3 to 15 mV, which corresponds to a potential difference between an intima and adventitia of a blood vessel.

When the dialysis device is configured to be worn on the human body, the positive electrode may be a surface electrode which is configured to be arranged in contact with the human body. When the dialysis device is configured to be implanted, the positive electrode may be provided on an outer casing of the dialysis device.

According to an embodiment, the dialyzer membrane is formed of silicon.

Silicon may be a suitable material for forming the dialyzer membrane, since silicon has low conductance and the membrane will therefore provide a lower conductance than blood and dialysate. This implies that a large electromagnetic field strength is provided across the pores of the membrane.

The dialyzer membrane may be formed by a silicon substrate. The forming of pores in the silicon substrate may be achieved using well-known and accurate semiconductor processing technology.

According to an embodiment, the dialyzer membrane is formed of a semiconductor substrate. Thus, the dialyzer membrane need not necessarily be formed of silicon, but other types of semiconductor substrates may be used while providing similar advantages as set out above for using a silicon membrane.

According to an embodiment, an integrated circuit is arranged on the dialyzer membrane.

Using a silicon or other semiconductor substrate, it is possible to also embed electronic circuitry on the substrate which provides the dialyzer membrane. Thus, the substrate may be used both for providing the dialyzer membrane and for carrying integrated circuit of the dialysis device, which may be particularly suitable for miniaturization of the dialysis device.

The integrated circuit may provide at least part of the electronic circuitry used for any of the functions of the dialysis device, such as control circuitry for the generator for generating electromagnetic fields for loosening electrostatic bonds between toxins and proteins.

The dialyzer membrane may be configured at a portion of a substrate that is arranged in the dialysis area to provide exchange of substances between blood flow and dialysate flow.

An integrated circuit may be provided on a different portion of the substrate, which may be arranged outside the dialysis area, so as not to be in contact with blood flow and/or dialysate flow. However, it should be realized that at least parts of the integrated circuit may be arranged within the dialysis area.

When the integrated circuit comprises a portion arranged outside the dialysis area, a seal is provided around the substrate to avoid any leakage of fluids from the dialysis area.

The use of the substrate both for providing an integrated circuit thereon and for providing the dialyzer membrane may also ensure that circuit lines are short, e.g. circuit lines of the generator for generating electromagnetic fields in the dialysis area for loosening electrostatic bonds between toxins and proteins. Short circuit lines may be advantageous in reducing stray electromagnetic fields being emitted by the dialysis device so as to avoid disturbance of any other equipment in the environment. The arrangement of the integrated circuit on the substrate providing the dialyzer membrane may thus allow for high field strengths between parallel plates of the generator with low stray fields outside.

According to a second aspect, there is provided a control system for blood dialysis, said control system comprising: an oscillator for generating an alternating electrical signal; two electrodes connected to the oscillator, which electrodes are configured for capacitive coupling to blood flow through a wall of a blood flow channel for providing an AC voltage based on the alternating electrical signal in the blood flow between the electrodes; an impedance measurement circuit, which is configured for measuring an impedance between the two electrodes at a plurality of frequencies, the measured impedances being indicative of a conductivity of blood; an electromagnetic field generating device configured to be capacitively coupled to the blood flow and dialysate flow in a dialysis area of a dialyzer, wherein the electromagnetic field generating device is configured to generate electromagnetic fields based on the alternating electrical signal in the dialysis area of the dialyzer for loosening electrostatic bonds between toxins and proteins in the blood flow.

Effects and features of this second aspect are largely analogous to those described above in connection with the first aspect. Embodiments mentioned in relation to the first aspect are largely compatible with the second aspect.

The control system may provide functionality for performing measurements on the blood flow involved in blood dialysis and may also provide functionality, e.g. by means of the generated electromagnetic field, to improve efficiency of the dialysis. The control system may be separate from circuitry, such as tubings etc., for providing blood flow and dialysate flow of the dialysis device. This implies that the control system may be installed for use with an existing dialysis device. However, it should be realized that the control system may alternatively be integrated in the dialysis device.

The control system may provide capacitive coupling of the AC voltage for performing impedance measurement to the blood flow in the blood flow channel. This implies that the electrodes may be arranged externally to the blood flow channel such that sterility is not compromised and easily enabling the measurement to be provided in an existing dialysis device.

The electromagnetic field generating device is also capacitively coupled to blood flow and dialysate flow such that the electromagnetic field for loosening electrostatic bonds between toxins and proteins in the blood flow may be easily provided to an existing dialysis device.

Thanks to the control system being able to be arranged completely externally to the blood flow and dialysate flow of a dialysis device, the control system may also be easily re-used in different dialysis devices.

The control system provides both measurements for monitoring the blood flow in the blood flow channel and functionality for improving efficiency of a dialysis device. This enables the control system gather information by measurements in order to base control of the dialysis on the gathered information.

By using the oscillator for generating electromagnetic fields for loosening electrostatic bonds between toxins and proteins in the blood flow and for generating an AC voltage for an impedance measurement, there is no need to have two separate oscillators. This enables a compact and cheap control system.

The control system may further comprise control circuitry, which may be commonly used for both generating electromagnetic fields for loosening electrostatic bonds between toxins and proteins in the blood flow and for generating an AC voltage for an impedance measurement, wherein the control circuitry is configured to generate a signal of a desired frequency in dependence of how the signal is to be used. For instance, the electromagnetic field generating device may be configured to provide electro-magnetic fields within a range of 100 kHz to 1 GHz, for example from 10 MHz to 500 MHz. In some embodiments, the generator may be configured to provide electro-magnetic fields within a range of 80 MHz to 170 MHz. The frequency of the AC voltage for the impedance measurement may be tuned in a range of 40 Hz to 110 MHz.

According to an embodiment, the control system may further comprise a first light source, which is configured to emit light into the blood flow channel and a second light source which is configured to emit second light into the blood flow channel, and a light detector, which is configured to detect first light from the first light source being diffusely transmitted through the blood flow and second light from the second light source being scattered by the blood flow.

The light sources and light detector may also be provided externally to the blood flow channel such that sterility is not compromised. This allows further measurements to be provided on the blood flow so as to allow gathering of more information relating to the blood flow by the control system. Thus, the control system also has more information available for improving control of a dialysis device.

The detection of first light being diffusely transmitted and second light being scattered may be used for determining a blood hematocrit level and/or a blood oxygenation level.

According to an embodiment, the control system further comprises a processor unit, which is configured to determine a blood hematocrit level based upon detected first light being diffusely transmitted and detected second light being scattered with compensation for an ion concentration in the blood based on the measured impedance, wherein the control system is further configured to provide a control signal for controlling a speed of fluid extraction in the dialyzer based on the blood hematocrit level.

Thus, the control system may comprise a processor unit for determining the blood hematocrit level within the control system. The processor unit may take into account the detected first light, the detected second light and an ion concentration based on the measured impedance by the impedance measurement circuit when determining the blood hematocrit level. Thus, by using both optical and electrical measurements, the control system may determine a blood hematocrit level with high accuracy.

The control system may further be able to provide control signals which may be used for controlling a dialysis device, e.g. for providing control of flowrate of blood flow and/or dialysate flow. The control system may for instance control a speed of fluid extraction across the dialyzer membrane based on the blood hematocrit level. If speed of fluid extraction is too high, the blood may be too thick (i.e. have too high blood hematocrit level).

According to an embodiment, the two electrodes are arranged on one or more conductive rings that are configured to be arranged around the blood flow channel, or as snap-on conductive planes on walls of a blood flow cassette.

This implies that the electrodes may be easily arranged in relation to the blood flow channel for providing impedance measurements on blood flow in the blood flow channel. The conductive rings may for instance be configured to be clipped onto the blood flow channel.

The electrodes may be arranged in relation to a blood flow cassette, in which a blood flow channel may be arranged. The electrodes may then be arranged as snap-on conductive planes, which may be easily arranged in relation to the blood flow channel According to an embodiment, the control system further comprises a laser light source which is configured to emit excitation light into the blood flow channel and a Raman spectrometer which is configured to detect Raman scattered light.

The laser light source and the Raman spectrometer may be arranged externally to the blood flow channel. The detection of Raman scattered light may be used for detecting presence and/or concentration of substances in the blood flow. Thus, the detection of Raman scattered light may be used for determining creatinine levels and/or other toxin levels in the blood flow.

The detection of Raman scattered light may be used in combination with other gathered information to monitor blood health and/or provide information on which control of dialysis is based.

According to an embodiment, the control system further comprises a control unit for controlling the oscillator and/or the electromagnetic field generating device for controlling the electromagnetic fields based on the alternating electrical signal in the dialysis area of the dialyzer.

The information gathered by the control system, e.g. by means of the impedance measurements, the detection of diffusely transmitted and scattered light and the detection of Raman scattered light, may be used by the control unit for controlling the electromagnetic fields for loosening electrostatic bonds between toxins and proteins. For instance, a frequency and/or amplitude of the electromagnetic field may be controlled to fit toxins present in the blood flow, which may be identified by the Raman spectrometer. Such control may ensure that unnecessary power consumption is avoided, as the electromagnetic field treatment may be optimized to the present toxins and concentration of toxins. This may improve battery life of the control system and a dialysis device, which may be particularly useful when the dialysis device is worn on or implanted in a human body.

According to an embodiment, the control system further comprises a processor unit, which is configured to process detected information, such as a measured impedance, and to determine blood health information based on the detected information, a memory, which is configured to store blood health information, and a wireless communication unit, which is configured to communicate blood health information to an external unit and/or configured to facilitate charging of an internal battery.

The control system may thus determine and store a history of blood parameters, which may be used in control of the dialysis device. The history of blood parameters may also be used in identifying abrupt changes or slow trends in blood parameters, which may be used in controlling the dialysis device and/or for providing alerts that other actions may be necessary, such as alerting a doctor or caregiver.

The wireless communication unit may ensure that blood health information is communicated to an external unit. This may allow blood health information to be communicated to a hospital to allow patient history to be available to a doctor or caregiver. The wireless communication unit may also or alternatively communicate information for external storage, such as storing information "in the cloud".

The wireless communication unit may also be used for wireless charging of an internal battery. However, it should also be realized that an internal battery may be wirelessly charged by a separate charging unit. Using wireless charging is advantageous to ensure that sterility is not compromised and is particularly advantageous for use when the dialysis device is implanted in a human body.

The control system may gather other information in addition to the blood health information, such as information relating to a technical condition of the dialysis device. Such information may also be stored in the memory and/or communicated to an external unit.

The processor unit configured to process detected information may for instance determine a blood hematocrit level, as described above. The control system may comprise a plurality of processor units which may be adapted to performing specific functions. Alternatively, the control system may comprise one processor unit, which may be provided with instructions for performing several different functions, such as executing different threads for simultaneously performing several functions.

According to an embodiment, at least the oscillator, the control unit, the processor unit, the memory and the wireless communication unit are arranged on a single integrated circuit.

This enables the control system to be miniaturized and very compact. This may be particularly useful when the control system is to be used with a dialysis device which is to be worn on or implanted in a human body.

According to an embodiment, the single integrated circuit may be arranged on a substrate providing a dialyzer membrane comprising pores for passing toxins in blood flow to dialysate flow through pores of the dialyzer membrane.

The arrangement of the single integrated circuit on the substrate, which also provides the dialyzer membrane may ensure that a very compact device may be provided for controlling and performing dialysis. The arrangement of the integrated circuit on the same substrate as the dialyzer membrane may ensure that a very short distance may be provided between electrodes for coupling the electromagnetic field into the dialysis area for loosening bonds between toxins and proteins. Such electrodes may be arranged on opposite sides of the pores. This ensures that a very high local field strength may be provided using a low voltage. Hence, disturbance of other equipment in the environment due to stray electromagnetic fields may be avoided. Also, since low voltages may be used, power consumption is limited. This may be useful in ensuring a prolonged battery life of the internal battery.

Also, the arrangement of the single integrated circuit on the substrate providing the dialyzer membrane may be useful for enabling stacking of dialysis sections. Two or more dialysis sections, each being able to provide exchange of substances between blood flow and dialysate flow, may be stacked having parallel substrates carrying integrated circuits and dialyzer membranes. Stacking of dialysis sections may provide for a very compact arrangement of a dialysis device with an improved dialysis capability (compared to a single dialysis section).

BRIEF DESCRIPTION OF THE DRAWINGS

The above, as well as additional objects, features and advantages of the present inventive concept, will be better understood through the following illustrative and non-limiting detailed description, with reference to the appended drawings. In the drawings like reference numerals will be used for like elements unless stated otherwise.

FIG. 1 is a schematic cross-sectional view of a dialysis device according to an embodiment, while schematically illustrating a control system of the dialysis device according to an embodiment.

DETAILED DESCRIPTION

Referring now to FIG. 1, a dialysis device 100 is schematically illustrated. The dialysis device 100 comprises a blood flow channel 102 for passing a blood flow therethrough and a dialysate flow channel 104 for passing a dialysate flow therethrough. The blood flow channel 102 and the dialysate flow channel 104 may provide blood flow and dialysate flow to a dialysis area 106 comprising a dialyzer membrane 110. The blood flow and dialysate flow are provided on opposite sides of the dialyzer membrane 110 for allowing exchange of substances between the blood flow and the dialysate flow through the dialyzer membrane 110. In particular, toxins may be filtered out of the blood flow by being passed through the dialyzer membrane 110 to the dialysate flow.

The dialysis device 100 may further comprise pumps and/or valves (not shown) for controlling blood flow and dialysate flow through the blood flow channel 102 and the dialysate flow channel 104, respectively.

The blood flow channel 102 may be configured to be connected to an artery of a human being for receiving blood to be dialyzed from the human being. The blood flow channel 102 may further be configured to be connected to a vein of the human being to pass blood having passed the dialysis area 106 back to the venous blood flow of the human being.

The dialysate flow channel 104 may be connected to a reservoir of dialysate for receiving dialysate to be transported to the dialysis area 106. The dialysate flow channel 104 may further be connected to a waste reservoir to which dialysate having passed the dialysis area 106 is transported together with waste products received from the blood flow.

The dialysis device 100 may be arranged external to a human being. A patient receiving dialysis treatment may then be regularly connected to the dialysis device 100 for removing toxins and other waste products from the blood of the patient.

Alternatively, the dialysis device 100 may be arranged to be worn on the human body or to be implanted in the human body. In such case, the dialysate may need to be re-used in order to avoid frequent exchange of the dialysate or avoid that the patient need to carry a large reservoir of dialysate. The re-use of the dialysate may be achieved using a module comprising cell culture-based bioreactors for filtering of the dialysate to remove waste products therefrom. When the dialysis device 100 is implanted, the waste products may be transported to the bladder such that the waste products may leave the human body through the urine. When the dialysis device 100 is worn on the human body, the waste products may be transported to a container, e.g. a bag, which the patient may empty regularly.

The dialysis device 100 may comprise an electromagnetic field generating device 120. The electromagnetic field generating device 120 may be capacitively coupled on opposite sides of the dialyzer membrane 110.

Thanks to using capacitive coupling, the electromagnetic field generating device 120 will not be in direct contact with either blood flow or dialysate flow. This implies that sterility is not compromised and that the electromagnetic field generating device 120 may be easily re-used for different patients.'

The electromagnetic field generating device 120 may comprise an oscillator 122, which provides an AC frequency signal for generating the electromagnetic field. The oscillator 122 may be tunable for tuning the frequency of the signal.

The electromagnetic field generating device 120 may further comprise a control circuitry 124 for controlling the signal being generated based on a signal from the oscillator 122. The control circuitry 124 may be controlled e.g. to provide a desired frequency of the signal and/or to provide a desired amplitude of the signal.

The control circuitry 124 may be controlled for generating an electromagnetic field having a constant frequency. However, according to an alternative, the control circuitry 124 may be controlled for varying the frequency of the electromagnetic field.

The electromagnetic field generating device 120 may further comprise a first coupler 126 and a second coupler 128, which are configured to be arranged on opposite sides of the dialyzer membrane 110. For instance, the first coupler 126 may be configured to be attached to a wall of the dialysis area 106 at a blood flow side of the dialysis area 106, whereas the second coupler 128 may be configured to be attached to a wall of the dialysis area 106 at a dialysate flow side of the dialysis area 106.

The first and second couplers 126, 128 may capacitively couple the signal received from the oscillator 122 and the control circuitry 124 into the dialysis area 106, through the blood flow, the dialyzer membrane 110 and the dialysate flow.

The first and second couplers 126, 128 may be implemented e.g. as coils, electrodes or capacitors. The generated electromagnetic field may be of a high frequency such that the first and second coupler 126, 128 may be high-frequency coils, high-frequency electrodes or high-frequency capacitors.

The dialyzer membrane 110 comprises pores 112, through which waste products in the blood flow may be passed for removing the waste products from the blood flow. The exchange of substances between the blood flow and the dialysate flow may mainly be controlled based on size of the pores 112, such that substances of small size may be passed from the blood flow to the dialysate flow.

Toxins in the blood flow have a small size so as to enable passing of the toxins from the blood flow to the dialysate flow. However, toxins may frequently be bound by electrostatic bonds to proteins having a larger size, preventing the protein-bound toxins to pass through the pores 112.

The electromagnetic field provided by the electromagnetic field generating device 120 may loosen the electrostatic bonds between toxins and proteins to ensure that the toxins pass through the dialyzer membrane 110.

The dialyzer membrane 110 may be formed of a material having lower conductance than blood and dialysate. This implies that an electromagnetic field strength between the first and second couplers 126, 128 may be larger across the dialyzer membrane 110 than in a bulk of the blood flow and the dialysate flow.

Thanks to the electromagnetic field strength being particularly strong at or around the pores 112 of the dialyzer membrane 110, the effect of loosening the electrostatic bonds between toxins and proteins may be particularly efficient at or around the pores 112. This implies that the toxins are not protein-bound at the location where the toxins need to pass through small-size pores 112 so as to provide a high efficiency of removing toxins from the blood flow.

The electromagnetic field generating device 120 may provide an electromagnetic field having a field strength of 100 V/m at the pores 112 of the dialyzer membrane 110.

The dialyzer membrane 110 may be formed from a semiconductor substrate, such as a silicon substrate.

Semiconductors may be suitable material for forming the dialyzer membrane 110, since semiconductors, such as silicon, has low conductance and the dialyzer membrane 110 will therefore provide a lower conductance than blood and dialysate.

This implies that a large electromagnetic field strength is provided across the pores 112 of the dialyzer membrane 110.

Further, using a semiconductor substrate for forming the dialyzer membrane 110 implies that the forming of pores in the substrate may be achieved using well-known and accurate semiconductor processing technology.

Using a semiconductor substrate, it is possible to also embed electronic circuitry on the substrate which provides the dialyzer membrane 110. Thus, the substrate may be used both for providing the dialyzer membrane 110 and for carrying integrated circuit of the dialysis device 100, which may be particularly suitable for miniaturization of the dialysis device 100.

When the membrane is formed from a semiconductor substrate, the capacitive couplers 126, 128 may be integrated on the same substrate as the pores 112. This implies that a distance between capacitive poles may be very small, such that a very low voltage provided by the electromagnetic field generating device 120 may produce large field strengths. For instance, a voltage of 1V across a 1 mm gap produces a field strength of 100 V/m. Thus, very large local field strengths may be provided without causing electromagnetic disturbance of any other equipment in the environment around the dialysis device 100.

The integrated circuit may provide at least part of the electronic circuitry used for any of the functions of the dialysis device 100, such as the oscillator 122 and the control circuitry 124 of the electromagnetic field generating device 120, and also other circuitry as will be discussed below.

The dialyzer membrane 110 may be formed at a portion of the substrate that is arranged in the dialysis area 106 to provide exchange of substances between blood flow and dialysate flow.

The integrated circuit may be provided on a different portion of the substrate, which may be arranged outside the dialysis area 106, so as not to be in contact with blood flow and/or dialysate flow. However, it should be realized that at least parts of the integrated circuit may be arranged within the dialysis area 106, i.e. within a space defined by walls surrounding the dialysis area 106.

When the integrated circuit comprises a portion arranged outside the dialysis area 106, a seal is provided around the substrate between the substrate and walls surrounding the dialysis area 106 to avoid any leakage of fluids from the dialysis area 106.

The dialysis device 100 may further comprise one or more sensors being used for gathering information relating to the blood flow. The gathered information may be used in a control unit 132, which may provide control of the dialyzer, such as controlling speed of blood flow and dialysate flow and/or for controlling parameters of the electromagnetic field used for loosening electrostatic bonds between toxins and proteins.

The gathered information may also provide indication of health status of a patient so as to allow monitoring of the patient. The gathered information may then be stored in a memory 134 and/or be communicated to an external unit.

The dialysis device 100 may comprise a control system 130 which may control functionality and gather information from the one or more sensors. The control system 130 may also comprise the control unit 132 and the memory 134. The control system 130 may further comprise a communication unit 136 for communicating with an external unit. The communication unit 136 may provide wireless communication, but it should be realized that wired communication may also or alternatively be provided.

The dialysis device 100 may further comprise an internal battery for providing power to components of the dialysis device 100. The internal battery may be wirelessly charged, e.g. via the wireless communication unit 136 or via a separate unit for wirelessly charging the battery. It should also be realized that in some embodiments, wired charging of the battery may be provided.

The control system 130 may be provided as a self-contained system, which may be detached from the dialyzer. Thus, the control system 130 may be installed on existing dialyzers for improving functionality of existing dialyzers. Also, the control system 130 may be separately manufactured, which may also simplify manufacturing of new dialysis devices 100. The one or more sensors of the control system 130 may perform measurements without being in contact with fluids of the dialysis device 100 in order to allow for detaching the control system 130 from the dialyzer without sterility being compromised. The control system 130 may thus be easily re-used between different dialysis devices 100.

However, as indicated above, electronic circuitry may be arranged on a common substrate with the dialyzer membrane 110. In such an implementation, the control system 130 may be integrated in the dialysis device 100.

Below, the control system 130 is further described, providing information of sensors that may be supported or included in the control system 130 and also further discussing the control of the dialysis device 100 provided by the control unit 132. It should be realized that the below description of the control system 130 may be applied either to a self-contained control system, which may be detached from the dialyzer or to a control system 130 being integrated in the dialysis device 100.

According to an embodiment, the control system 130 may be configured to perform impedance measurements.

The control system 130 may thus comprise two capacitive electrodes 140, 142, which are configured for capacitive coupling to the blood flow in the blood flow channel 102.

The capacitive electrodes 140, 142 may be configured, according to different embodiments, to be arranged in various relations to the blood flow channel 102. The capacitive electrodes 140, 142 may provide a capacitive coupling to the blood flow through a wall of the blood flow channel 102 for providing a coupling to the blood flow without the capacitive electrodes 140, 142 being in direct contact with blood flow.

For instance, the capacitive electrodes 140, 142 may be arranged on opposite sides of a cross-section of the blood flow channel 102. Thus, a conductivity of blood may be measured across a cross-section of the blood flow channel 102. The capacitive electrodes 140, 142 may for instance be arranged on an annular carrier, which may be arranged around the blood flow channel 102, wherein the electrodes 140, 142 are arranged on diametrically opposite locations of the annular carrier to be arranged on opposite sides of the cross-section of the blood flow. The annular carrier may be provided with a releasable lock such that the annular carrier may e.g. be clipped on the blood flow channel 102.

According to an alternative, the capacitive electrodes are arranged at different positions in relation to the blood flow, one electrode 142 being downstream to another electrode 140. Thus, a conductivity may be measured along a direction of the blood flow. Each of the electrodes 140, 142 may be arranged in relation to the blood flow channel 102 as described above and as illustrated in FIG. 1. The electrodes 140, 142 may be provided in form of conductive rings, which are configured to be arranged around the blood flow channel 102.

The control system 130 further comprises a generator 144, which is configured for generating an AC voltage between the two capacitive electrodes 140, 142. The generator 144 may use the oscillator 122, which is also used by the electromagnetic field generating device 120. Further, the generator 144 may use the control circuitry 124 and adapt the function of the control circuitry 124 for enabling output of the desired AC voltage signal from the control circuitry 124 to the electrodes 140, 142.

The generator 144 may be configured to generate a tunable frequency AC voltage for enabling an impedance spectroscopy measurement to be performed. For instance, the frequency of the AC voltage may be tuned in a range of 40 Hz to 110 MHz.

The signal provided to the electrodes 140, 142 may generate an electrical current in the blood flow. This electrical current may be detected using capacitive coupling to capacitive electrodes as a voltage signal between two capacitive electrodes. The capacitive electrodes may be connected to an impedance measurement circuit 146, which may use the detected signal to determine an impedance of the blood flow in the blood flow channel 102.

The impedance measurement circuit 146 may receive a signal detected by the same capacitive electrodes 140, 142 which are also used for providing the AC voltage from the generator 144 into the blood flow. However, it should be understood that the impedance measurement circuit 146 may alternatively receive a signal from two other capacitive electrodes.

As mentioned above, the frequency of the AC voltage may be tuned. Thus, the impedance measurement circuit 146 may be used for performing an impedance spectroscopy measurement on the blood flow.

The impedance measurement performed by the impedance measurement circuit 146 may be further transferred to a processor unit 138, which may be configured to analyze the impedance measurement. The processor unit 138 may for instance be configured to determine concentrations of ions, such as sodium, in the blood flow based on the impedance measurement.

As shown in FIG. 1, the impedance measurement may be performed on blood flow before the blood flow reaches the dialysis area 106. However, it should be realized that additionally or alternatively impedance measurements may be performed at other locations in the dialysis device 100. For instance, impedance measurements may also be performed on blood flow after the blood flow has passed the dialysis area 106 and impedance measurements may also be performed on dialysate flow before the dialysate flow reaches the dialysis area 106 and/or after the dialysate flow has passed the dialysis area 106.

Performing measurements before and after the dialysis area 106 may be used for analyzing how the ion concentration in the blood flow and/or dialysate flow is changed in the dialysis area 106.

According to an embodiment, the control system 130 may be configured to perform light detection measurements.

The control system 130 may thus further comprise a first light source 150 and a second light source 152, which are configured to emit first light and second light, respectively into the blood flow channel 102. The control system 130 may further comprise a light detector 154, which is configured to detect light originating from the first light source 150 and the second light source 152. Alternatively, the control system 130 may comprise a first and a second light detector, which are each dedicated for detecting light originating from the first light source 150 and the second light source 152, respectively. The first and second light sources 150, 152 are arranged in relation to a common cross-section of the blood flow channel 102 so as to interact with a common portion of the blood flow.

The first light source 150 and the light detector 154 may be arranged on opposite sides of a cross-section of the blood flow channel 102. The light detector 154 may thus be configured to detect first light being diffusely transmitted through the blood flow.

The second light source 152 may be arranged to emit light into the cross-section of the blood flow channel 102 such that no part of a light beam of the second light reaches the light detector 154. The second light will be scattered by particles in the blood flow and the light detector 154 is thus configured to only detect scattered second light.

The second light source 152 may be arranged in relation to the first light source 150 such that a propagation direction of a light beam of the first light will be perpendicular to a propagation direction of a light beam of the second light. However, it should be understood that the propagation directions of the light beams need not be exactly perpendicular. It may be sufficient that the second light source 152 is arranged such that the light beam of the second light is not incident on the light detector 154 and that only second light being scattered into propagating in a different direction will reach the light detector 154.

The light detector 154 may thus provide a measurement of an intensity of diffusely transmitted light through the blood flow and an intensity of scattered light by the blood flow.

The light detector 154 may be configured to detect an intensity of light incident on the light detector 154. The light detector 154 may thus comprise a single photo-sensitive area, which may convert an intensity of incident light to an electrical signal for reading out the intensity of light. However, the light detector 154 may comprise a plurality of photo-sensitive areas, which may be associated with different filters for detecting intensity of incident light of different wavelengths.

The first and second light sources 150, 152 may be light-emitting diodes (LEDs), which may be configured to emit light of a relatively narrow wavelength. However, it should be realized that the light sources 150, 152 may emit a broad range of wavelengths, wherein the light detector 154 may be a spectrally resolved detector. When the first and second light is of a common wavelength, a single LED may be used and may be associated with different waveguides (forming the first and second light sources 150, 152) for providing emission of light from different positions into the blood flow channel 102.

The first light source 150, the second light source 152 and the light detector 154 may be arranged on a common annular carrier, which may be arranged around the blood flow channel 102, wherein the first light source 150, the second light source 152 and the light detector 154 are arranged in different locations of the annular carrier for ensuring that the light detector 154 detects diffusely transmitted first light and scattered second light. The annular carrier may be provided with a releasable lock such that the annular carrier may e.g. be clipped on the blood flow channel.

The scattering of light may be relatively independent on what type of particle is scattering light, whereas diffuse transmittance may be dependent on whether the light is absorbed by a specific type of particle. Thus, by selecting a wavelength of the first light to coincide with a high absorption of a specific type of particle of interest, the relation between the scattered light and the diffusely transmitted light may be used for determining a concentration of a specific type of particle in the blood flow. For instance, this may be used for determining a blood hematocrit level and/or a blood oxygenation level. In determination of blood oxygenation level, using two or even more different wavelengths may be particularly advantageous for providing a reliable measurement.

The first light and the second light may use a common wavelength, such that the detection of first light and second light may be performed sequentially. However, since intensity of scattering of light may be relatively similar for different wavelengths, the second light may use a different wavelength than the first light. In such case, the light detector 154 may also comprise two different light-detecting elements associated with different filters, such that the diffusely transmitted first light and the scattered second light may be detected simultaneously.

For detection of blood hematocrit level and/or blood oxygenation level, the first light may for instance be a wavelength in a range of 630-670 nm and the second light may for instance be a wavelength in a range of 800-980 nm.

The first and second light sources 150, 152 and the light detector 154 may also be used for detecting optical absorption and/or scattering of light at a plurality of different wavelengths, e.g. in ranges of ultraviolet light, visible light and/or infrared light. The detected light intensities may be used for determining concentration levels of various different particles and/or substances in the blood flow. The first and second light sources 150, 152 may in this respect emit broadband wavelengths of light and the light detector 154 may comprise filters for detecting intensities of respective wavelengths of light. Alternatively, a wavelength of light emitted by the first and/or the second light source 150, 152 may be tuned for sequentially emitting different wavelengths of light.

The light sources 150, 152 may receive control signals, e.g. from the control unit 132, for triggering emission of light and/or controlling a wavelength emitted by the light sources 150, 152.

The light detector 154 may also receive control signals, e.g. from the control unit 132, for triggering detection of light and/or read-out of detected light from the light detector 154.

The light detection measurements performed by the light detector 154 may be further transferred to the processor unit 138, which may be configured to analyze the light detection measurements. The processor unit 138 may for instance be configured to determine blood hematocrit and/or blood oxygenation levels based upon detected first light being diffusely transmitted and detected second light being scattered. The processor unit 138 may further take an ion concentration determined by the impedance measurement into account when determining blood hematocrit and/or blood oxygenation levels such that the blood hematocrit and/or blood oxygenation levels may be compensated for an ion concentration in the blood based on the measured impedance.

As shown in FIG. 1, the light detection measurement may be performed on blood flow before the blood flow reaches the dialysis area 106. However, it should be realized that additionally or alternatively light detection measurements may be performed at other locations in the dialysis device 100. For instance, light detection measurements may also be performed on blood flow after the blood flow has passed the dialysis area 106 and light detection measurements may also be performed on dialysate flow before the dialysate flow reaches the dialysis area 106 and/or after the dialysate flow has passed the dialysis area 106.

Performing measurements before and after the dialysis area 106 may be used for analyzing e.g. how the blood hematocrit level and/or the blood oxygenation level in the blood flow is changed in the dialysis area 106.

According to an embodiment, the control system 130 may be configured to perform measurements of Raman scattered light.

The control system 130 may thus further comprise a laser light source 160 which is configured to emit excitation light into the blood flow channel 102 and a Raman spectrometer 162 which is configured to detect Raman scattered light.

The laser light source 160 and the Raman spectrometer 162 may be arranged externally to the blood flow channel 162, such that light from the laser light source 160 may be transmitted through a wall of the blood flow channel 102 and light is detected by the Raman spectrometer 162 through a wall of the blood flow channel 102.

The laser light source 160 and the Raman spectrometer 162 may be arranged on diametrically opposite locations to a cross-section of the blood flow channel 162. However, since the Raman spectrometer 162 is configured to detect scattered light, the laser light source 160 and the Raman spectrometer 162 may be arranged in any angular relation to the cross-section of the blood flow channel 102.

The laser light source 160 and the Raman spectrometer 162 may be arranged on a common annular carrier for being arranged around a cross-section of the blood flow channel 102, similar to the annular carriers discussed above for other sensors. However, the laser light source 160 and the Raman spectrometer 162 may alternatively be separately arranged in relation to the blood flow channel 102, e.g. using adhesive surfaces for arranging the laser light source 160 and the Raman spectrometer 162 in relation to the blood flow channel 102.

The Raman scattered light detection measurements performed by the Raman spectrometer 162 may be further transferred to the processor unit 138, which may be configured to analyze the Raman scattered light detection measurements. The processor unit 138 may for instance be configured to determine presence and/or concentration of substances in the blood flow based upon the detected Raman scattered light. Thus, the detection of Raman scattered light may be used for e.g. determining creatinine levels and/or other toxin levels in the blood flow.

As shown in FIG. 1, the Raman scattered light detection measurement may be performed on blood flow before the blood flow reaches the dialysis area 106. However, it should be realized that additionally or alternatively Raman scattered light detection measurements may be performed at other locations in the dialysis device 100. For instance, Raman scattered light detection measurements may also be performed on blood flow after the blood flow has passed the dialysis area 106 and Raman scattered light detection measurements may also be performed on dialysate flow before the dialysate flow reaches the dialysis area 106 and/or after the dialysate flow has passed the dialysis area 106.

Performing measurements before and after the dialysis area 106 may be used for analyzing e.g. presence and/or concentration of substances in the blood flow and/or dialysate flow before and after the dialysis area 106.

As described above, the processor unit 138 may be configured to receive measurements from one or more sensors. The processor unit 138 may thus analyze and determine parameters relating to a condition of the patient on which dialysis treatment is performed.

The processor unit 138 may create a history of parameters, such that an evolvement or change of parameters may be followed, e.g. to detect sudden changes and/or slow trends. The determined parameters by the processor unit 138 may be stored in the memory 134, storing the history of parameters.

The processor unit 138 may determine blood flow and/or dialysate flow parameters, which may be used for controlling dialysis by the dialysis device 100. Such parameters may be blood hematocrit level and/or blood oxygenation level, ion concentrations, presence and/or concentrations of particular toxins or other substances in the blood flow. The parameters may also relate to concentrations or levels before and after the dialysis in the dialysis area 106, which may define an efficiency of the dialysis.

The processor unit 138 may provide control signals based on the parameters for controlling the dialysis. The control signals may be transmitted to the control unit 132, which may execute control of the dialysis, such as controlling a speed of blood flow and/or dialysate flow and controlling an amplitude and frequency of the electromagnetic field generated by the electromagnetic field generating device 120.

Alternatively, the processor unit 138 may transmit parameter values to the control unit 132, which may take decisions for controlling dialysis based on the parameter values.

The control unit 132 and/or the processor unit 138 may for instance be configured to control a speed of blood flow through the dialysis area 106 in dependence of a blood hematocrit level to avoid that fluid extraction is performed too quickly giving too thick blood.

The control unit 132 and/or the processor unit 138 may control a frequency and/or amplitude of the electromagnetic field to fit toxins present in the blood flow, which may be identified by the Raman spectrometer 162. Such control may ensure that unnecessary power consumption is avoided, as the electromagnetic field treatment may be optimized to the present toxins and concentration of toxins.

The processor unit 138 may create blood health information based on the measurements by the one or more sensors. The blood health information may provide an indication of blood health of the patient. The blood health information may be used to trigger an alert when an action is necessary, e.g. by a doctor or a caregiver. The blood health information may also be stored for later analysis allowing a doctor or caregiver to follow development of functionality of the dialysis of a patient. This is of particular interest when the dialysis device 100 is worn on or implanted in the human body, such that blood health information may be continuously acquired.

The control system 130 may also be configured to determine information relating to the dialysis device 100, such as parameters defining a technical condition of the dialysis device 100. Thus, functionality of pumps/valves may be monitored and channels within the dialysis device 100 may be monitored to determine if the channels are being clogged. Such information relating to the dialysis device 100 may also be determined by the processor unit 138 receiving measurements from sensors. The processor unit 138 may provide alerts based on detecting malfunctioning parts to trigger maintenance of the dialysis device 100.

The control system 130 may be configured to communicate information to an external unit via the communication unit 136. This may be of particular interest when the dialysis device 100 is worn on or implanted in a human body, as the control system 130 may then communicate information allowing remotely placed doctors/caregivers to be informed of health of a patient and/or to determine whether any actions are needed.

The communication of information may be triggered by alerts created by the processor unit 138. However, the communication unit 136 may alternatively or additionally be configured to regularly communicate information to the external unit.

The processor unit 138 and/or the control unit 132 may be implemented as one or more general-purpose processing units, such as a central processing unit (CPU), which may execute instructions of one or more computer programs in order to implement functionality of the processor unit 138.

The functionality of the processor unit 138 and the control unit 132 may be implemented as separate threads within a common general-purpose processing unit.

The processor unit 138 and/or the control unit 132 may alternatively be implemented as firmware arranged e.g. in an embedded system, or as a specifically designed processing unit, such as an Application-Specific Integrated Circuit (ASIC) or a Field-Programmable Gate Array (FPGA), which may be configured to implement functionality of the processor unit 138.

According to an embodiment, control components of the control system 130 may be arranged on a single chip. Thus, the control unit 132, the memory 134, the communication unit 136 and the processor unit 138 may be arranged on a common, single chip. Also, the oscillator 122 and the control circuitry 124 used by the electromagnetic field generating device 120 and the generator 144 for generating an AC voltage for impedance measurements may be arranged on the single chip. The chip may also include circuitry for controlling the one or more sensors and for reading out signals from the one or more sensors.

According to an embodiment, the single chip may also include the dialyzer membrane 110, which may be formed in a semiconductor substrate as described above.

It should however be realized that, even though arranging components on a common, single chip may be advantageous for providing a compact control system 130, various components could be arranged in separate physical units, such as on separate chips, e.g. in a hybrid stack.

According to an embodiment, the dialysis device 100 further comprises a DC generator 170, which is configured for generating an electrostatic direct current field between the blood flow in the dialyzer and the human body, where a negative electrode 172 of the DC generator is configured to be arranged at a blood flow side of the dialyzer and a positive electrode 174 of the DC generator is configured to be arranged in contact with the human body.

The use of an electrostatic direct current field may prevent coagulation of blood. Blood components, such as platelets, red blood cells and white blood cells may be negatively charged, and the negative charge may be used by the body for holding the blood components at an injury site to cause coagulation. By providing an electrostatic direct current field in the blood flow of the dialysis device 100, blood components may be forced to move with the blood flow so as to prevent coagulation of blood in the blood flow of the dialysis device. This may be particularly useful to avoid clogging of blood flow channels 102 of the dialysis device 100.

The use of the electrostatic direct current field may be particularly advantageous when the dialysis device is to be worn on or implanted in a human body, since the dialysis device is to be used for a long period of time. However, it should be realized that the electrostatic direct current field may also be used with other dialysis devices 100.

The electrostatic direct current field may be configured to provide a potential difference in a range of 3 to 15 mV, which corresponds to a potential difference between an intima and adventitia of a blood vessel.

When the dialysis device 100 is configured to be worn on the human body, the positive electrode 174 may be a surface electrode which is configured to be arranged in contact with the human body. When the dialysis device 100 is configured to be implanted, the positive electrode 174 may be provided on an outer casing of the dialysis device 100.

In the above the inventive concept has mainly been described with reference to a limited number of examples. However, as is readily appreciated by a person skilled in the art, other examples than the ones disclosed above are equally possible within the scope of the inventive concept, as defined by the appended claims.

The invention claimed is:

1. A dialysis device comprising:
   a. A dialyzer for exchange of substances between a blood flow and a dialysate flow in a dialysis area of the dialyzer, wherein the dialyzer comprises a dialyzer membrane for passing toxins in the blood flow to the dialysate flow through pores of the dialyzer membrane; and
   b. A capacitively coupled generator for generating electromagnetic fields in the dialysis area for loosening electrostatic bonds between toxins and proteins in the blood flow, wherein the generator is capacitively coupled to the blood flow and to the dialysate flow on opposite sides of the dialyzer membrane, and wherein the dialyzer membrane is formed of one or more semiconductor materials having lower conductance than blood and dialysate such that a large electromagnetic field strength is provided across the pores of the dialyzer membrane.

2. The dialysis device according to claim 1, further comprising:
   two capacitive electrodes which are configured for capacitive coupling to the blood flow through a wall of a blood flow channel configured to pass the blood flow therethrough;
   a generator which is configured for generating an AC voltage between the two capacitive electrodes; and
   an impedance measurement circuit, which is configured for measuring an impedance between the two electrodes at a plurality of frequencies, the measured impedances being indicative of a conductivity of blood.

3. The dialysis device according to claim 2, further comprising:
   a first light source, which is configured to emit first light into the blood flow channel, wherein the emitted light is directed towards a light detector, which is arranged on an opposite side of the blood flow channel from the first light source, the light detector being configured to detect first light from the light source being diffusely transmitted through the blood flow;
a second light source, which is configured to emit second light into the blood flow channel, wherein the second light source is arranged in relation to the light detector and the blood flow channel such that only scattered second light reaches the light detector; and
a processor, which is configured to determine blood hematocrit and/or blood oxygenation levels based upon detected first light being diffusely transmitted and detected second light being scattered with compensation for an ion concentration in the blood based on the measured impedance.

4. The dialysis device according to claim 2, wherein the generator for generating electromagnetic fields for loosening electrostatic bonds between toxins and proteins in the blood flow and the generator which is configured for generating an AC voltage between the two capacitive electrodes use a common oscillator.

5. The dialysis device according to claim 1, wherein the dialysis device is configured for being worn on or implanted in a human body.

6. The dialysis device according to claim 5, further comprising a DC generator, which is configured for generating an electrostatic direct current field between the blood flow in the dialyzer and the human body, where a negative electrode of the DC generator is configured to be arranged at a blood flow side of the dialyzer and a positive electrode of the DC generator is configured to be arranged in contact with the human body.

7. The dialysis device according to claim 1, wherein the dialyzer membrane is formed of silicon.

8. The dialysis device according to claim 7, wherein an integrated circuit is arranged on the dialyzer membrane.

9. The dialysis device according to claim 2, further comprising:
a control system for blood dialysis, said control system comprising:
the generator;
the two capacitive electrodes; and
the impedance measurement circuit.

10. The dialysis device according to claim 9, wherein the control system further comprises:
a first light source, which is configured to emit light into the blood flow channel and a second light source which is configured to emit second light into the blood flow channel; and
a light detector, which is configured to detect first light from the first light source being diffusely transmitted through the blood flow and second light from the second light source being scattered by the blood flow.

11. The dialysis device according to claim 10, wherein the control system further comprises a processor unit, which is configured to determine a blood hematocrit level based upon detected first light being diffusely transmitted and detected second light being scattered with compensation for an ion concentration in the blood based on the measured impedance, wherein the control system is further configured to provide a control signal for controlling a speed of fluid extraction in the dialyzer based on the blood hematocrit level.

12. The dialysis device according to claim 9, wherein the two electrodes are arranged on one or more conductive rings that are configured to be arranged around the blood flow channel, or as snap-on conductive planes on walls of a blood flow cassette.

13. The dialysis device according to claim 9, wherein the control system further comprises a laser light source which is configured to emit excitation light into the blood flow channel and a Raman spectrometer which is configured to detect Raman scattered light.

14. The dialysis device according to claim 9, wherein the control system further comprises a control unit for controlling the generator for controlling electromagnetic fields based on the generated AC voltage in the dialysis area of the dialyzer.

15. The dialysis device according to claim 14, wherein the control system further comprises:
a processor unit, which is configured to process detected information, such as a measured impedance, and to determine blood health information based on the detected information;
a memory, which is configured to store blood health information; and
a wireless communication unit, which is configured to communicate blood health information to an external unit and/or configured to facilitate charging of an internal battery.

16. The dialysis device according to claim 15, wherein at least the generator, the control unit, the processor unit, the memory and the wireless communication unit are arranged on a single integrated circuit.

17. The dialysis device according to claim 16, wherein the single integrated circuit is arranged on a substrate providing the dialyzer membrane.

* * * * *